United States Patent [19]

Cleveland, Jr. et al.

[11] Patent Number: 5,467,223

[45] Date of Patent: Nov. 14, 1995

[54] DRAPE ADAPTER

[75] Inventors: John T. Cleveland, Jr.; Benjamin M. Rubin, both of Jacksonville, Fla.

[73] Assignee: Xomed-Treace Inc., Jacksonville, Fla.

[21] Appl. No.: 168,801

[22] Filed: Dec. 16, 1993

[51] Int. Cl.$^6$ ............................ G03B 11/04; B65D 85/38
[52] U.S. Cl. ............................ 359/510; 359/511; 359/900
[58] Field of Search ............................ 359/507, 510, 359/511, 512, 900; 206/316.1, 316.3

[56] References Cited

U.S. PATENT DOCUMENTS

| | | | |
|---|---|---|---|
| 3,698,791 | 10/1972 | Walchle et al. | 359/510 |
| 3,796,477 | 3/1974 | Geraci | 359/511 |
| 4,266,663 | 5/1981 | Geraci | 359/510 |
| 4,799,779 | 1/1989 | Mesmer | 359/510 |
| 5,311,358 | 5/1994 | Pederson et al. | 359/510 |

*Primary Examiner*—Paul M. Dzierzynski
*Assistant Examiner*—James Phan
*Attorney, Agent, or Firm*—Baker & Botts

[57] ABSTRACT

The adapter member for a microscope cooperates with a universal microscope drape having a universal positioning member. The adapter member is detachably secured to the lens housing of a microscope in tandem with a lens unit located in the lens housing. The adapter member is free from connection with the lens unit and can be installed without disassembling the lens housing. In one embodiment of the invention, the adapter member is threaded to the lens housing and in another embodiment of the invention the adapter member is secured to the lens housing with set screws. The adapter member has a universal engagement portion that is engagable with the universal positioning member of the universal microscope drape. A different adapter member is provided for each differently manufactured microscope but each different adapter member has the same universal engagement portion. Thus the same microscope drape can be used to cover differently manufactured microscopes of the same general size and shape.

18 Claims, 5 Drawing Sheets

FIG. 8
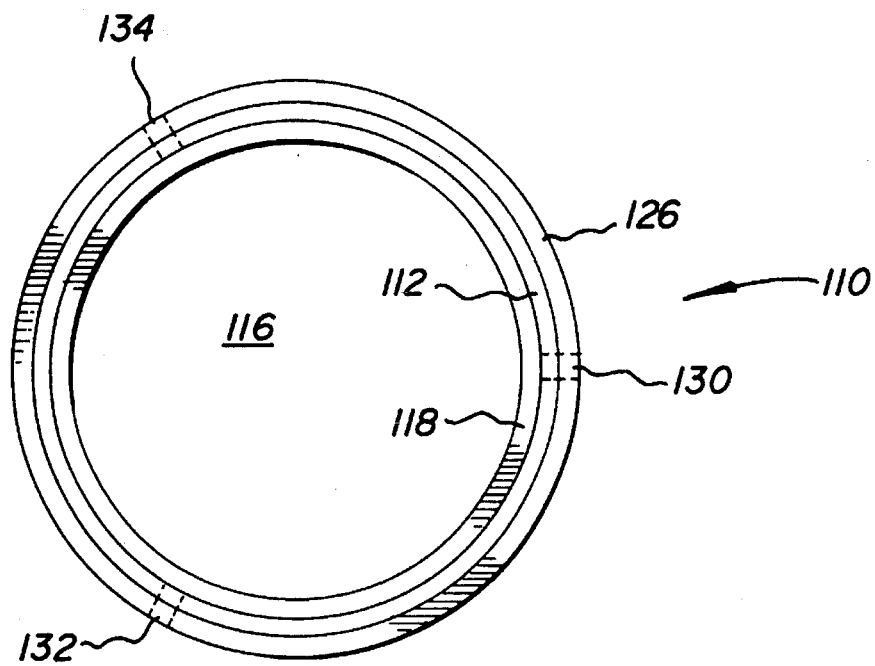
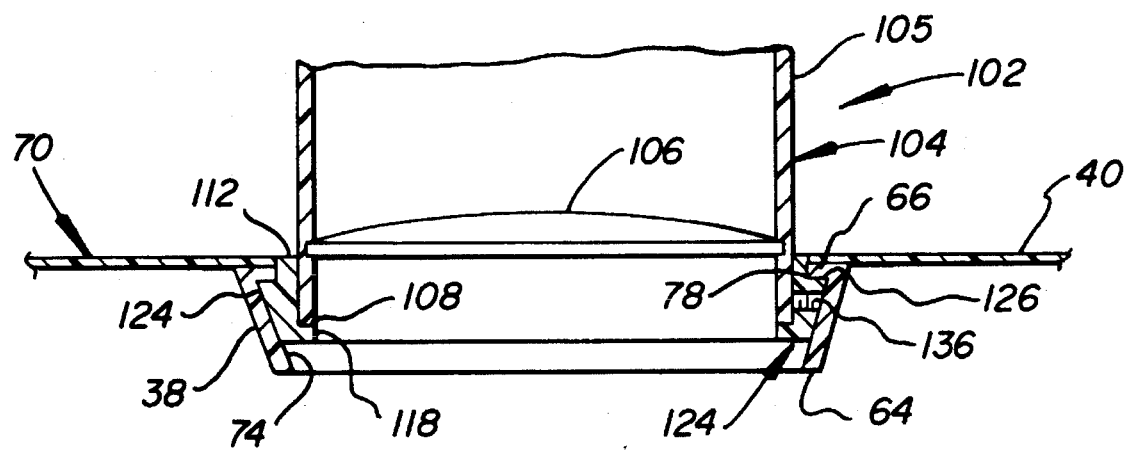
FIG. 9

DRAPE ADAPTER

BACKGROUND OF THE INVENTION

This invention relates to microscope drape positioning systems employing a universal drape, and more particularly to a novel drape adapter that permits use of a universal drape without disassembling any part of the microscope.

Microscopes used in performing surgery are generally permanent fixtures in an operating room. The relatively large size of the microscope and its structural complexity makes it difficult to sterilize the microscope each time a surgery is performed. Thus it is common practice before each surgical procedure to cover the surgical microscope with a disposable sterile drape.

A microscope drape is often initially affixed to the microscope at the lens housing for the objective lens, to orient the drape with respect to other structure of the microscope. For example, a microscope drape such as shown in U.S. Pat. No. 4,799,779 includes an annular positioning sleeve attached to a cover member of the drape. The positioning sleeve is adapted to fit onto the objective lens housing of the microscope to initially affix the microscope drape to the microscope. Once the microscope drape is attached to the objective lens housing, other portions of the drape can be conveniently spread and positioned to cover the remainder of the microscope structure.

To ensure that the microscope drape forms a sterile barrier between the microscope and the operating room, it is desirable that the positioning sleeve tightly grip the objective lens housing and that other portions of the microscope drape including the cover member be arranged on the microscope as a protective enclosure.

It has been found that the objective lens housing for comparable microscopes of different manufacture are often of different size. Thus a microscope drape positioning sleeve that tightly grips the lens housing of one microscope may not tightly grip the lens housing of a similar size microscope made by another manufacturer. Consequently, a microscope drape designed for one manufacturer's microscope is usually not feasible for draping a second manufacturer's microscope since an insecure fit of the positioning sleeve on the second manufacturer's lens housing can compromise the sterile barrier provided by the drape. Also, an ill fitting positioning sleeve of the drape that slips away from the objective lens housing during surgery may impede the surgeon's view or necessitate interruption of the surgery to resecure the positioning sleeve.

Thus, to ensure compatibility between the microscope and the microscope drape, it is customary to manufacture microscope drapes with positioning sleeves of different size that can be selected to provide a snug fit on the lens housings of different microscope manufacturers.

Thus, manufacturers of microscope drapes, and hospitals which stock such microscope drapes, must keep separate inventories of microscope drapes for each differently manufactured microscope that is used in a surgical facility.

If the supply of microscope drapes for a microscope of one manufacturer becomes depleted, an operating room may be rendered unusable while awaiting resupply of the correct drape for the microscope.

It is thus desirable to provide a positioning system for a microscope drape that permits use of the same microscope drape with the same positioning sleeve on a variety of different microscopes having different lens housings without the need to disassemble any part of the microscope.

OBJECTS AND SUMMARY OF THE INVENTION

Among the several objects of the invention may be noted the provision of a novel microscope drape positioning system, a novel microscope drape positioning system that permits use of a universal drape for a variety of microscopes of different manufacturers, a novel microscope adapter for a universal microscope drape, and a novel method of draping a microscope.

Other objects and features of the invention will be in part apparent and in part pointed out hereinafter.

In accordance with the present invention, the microscope drape positioning system is directed to microscopes of different manufacturers having different objective lens housings.

An adapter member for a microscope of one specific manufacturer is detachably secured to the objective lens housing of the microscope.

The adapter member is formed with a universal engaging portion that is of complementary shape with a universal positioning member of the microscope drape.

The adapter member can be threaded to existing threads in the objective lens housing without disassembling the lens housing. As a further option, the adapter member can be secured to the outer periphery of the objective lens housing with set screws, for example, and thus avoid disassembly of the lens housing.

Preferably, the universal engagement portion of the adapter member has the profile of an outer surface of a frustum of a cone. An engagement portion of the microscope drape positioning member is of complementary shape and has the profile of the inner surface of a hollow frustum of a cone. The inner engagement surface of the drape positioning member is mounted upon the outer engagement surface of the adapter member to form a secure but detachable joint.

Since the microscope drape positioning member is not directly attached to the objective lens housing, the previous need for providing a direct custom fit between the microscope drape positioning member and the objective lens housing is avoided.

In accordance with the invention, each differently manufactured microscope is provided with its own specific adapter member. Thus microscopes of different manufacture may have their own distinct adapter members. However, each different adapter member is formed with the same universal engagement portion to mate with the same corresponding universal engagement portion of the microscope drape positioning member.

The microscope drape is thus a universal microscope drape because the universal positioning member of the microscope drape matches the universal engagement portion of each different adapter member. Advantageously, the universal microscope drape with the universal positioning member can be used to cover a variety of differently manufactured microscopes of the same general size and shape regardless of any differences in the lens housings.

The invention accordingly comprises the constructions and method hereinafter described, the scope of the invention being indicated in the claims.

DESCRIPTION OF THE DRAWINGS

In the accompanying drawings,

FIG. 8 is a plan view of the adapter member of the positioning system shown in FIG. 7;

FIG. 9 is a sectional view of the positioning system as installed on a microscope;

Corresponding reference characters indicate corresponding parts throughout the several views of the drawings.

DETAILED DESCRIPTION OF THE INVENTION

Figure 1:
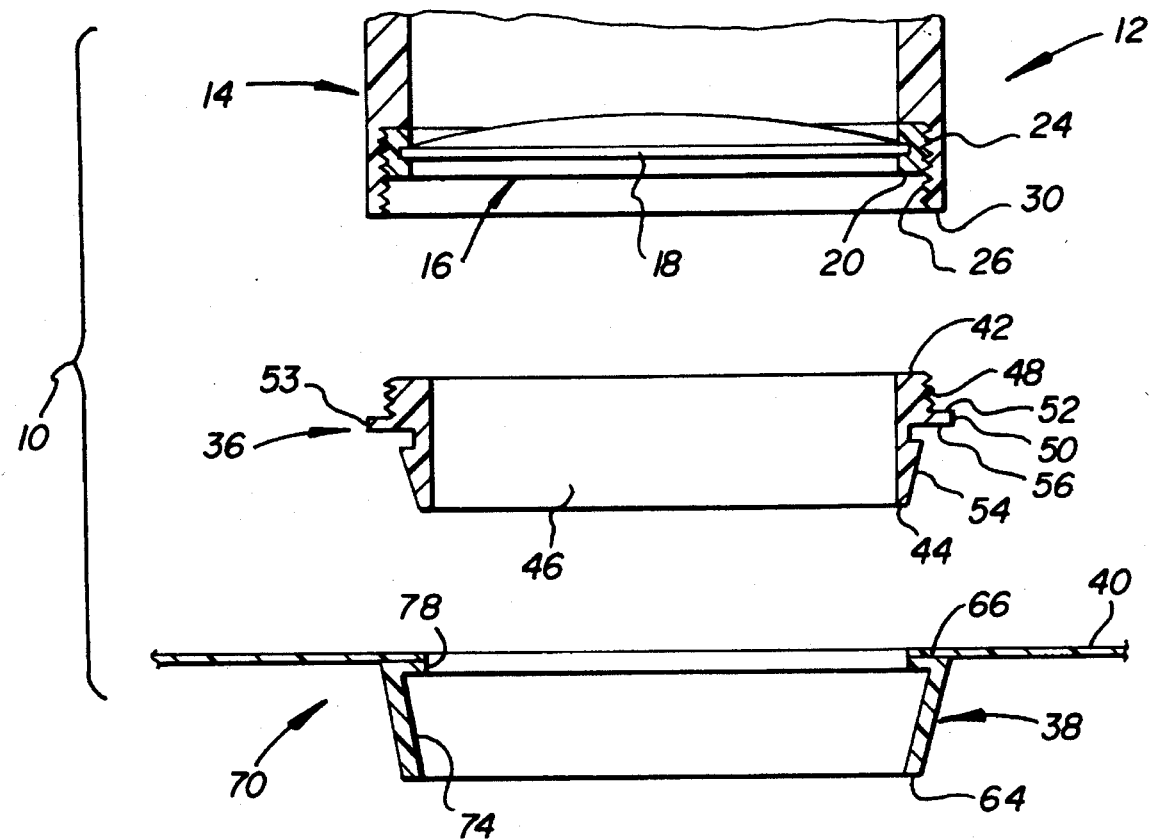
FIG. 1 is an exploded sectional view of a positioning system for a microscope drape, incorporating one embodiment of the invention, prior to installation on a microscope of a first manufacturer.
Figure 2:
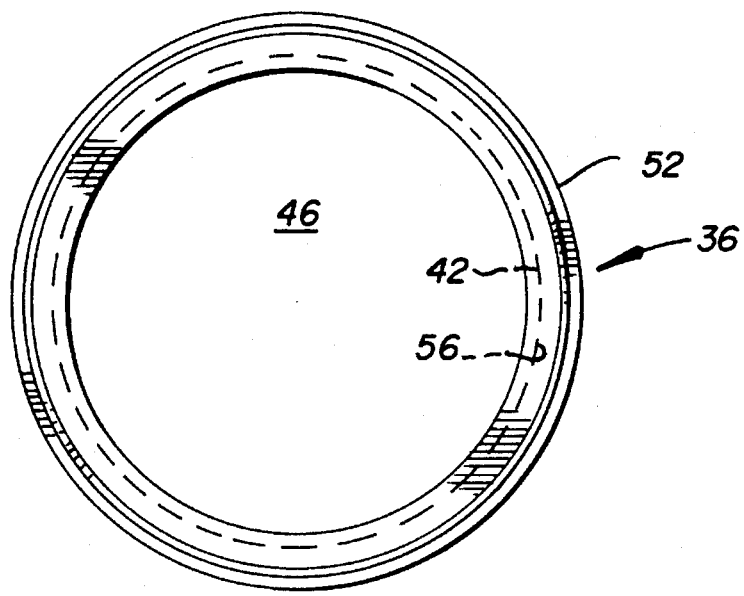
FIG. 2 is a plan view of the adapter member of the positioning system shown in FIG. 1.
Figure 3:
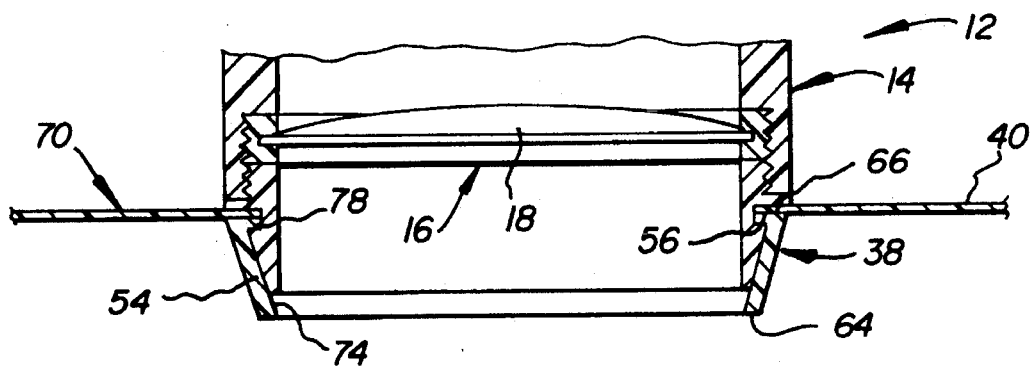
FIG. 3 is a sectional view of the positioning system as installed on a microscope.

A positioning system for microscope drapes incorporating a preferred embodiment best mode of the invention is generally indicated by the reference number 10 in FIG. 1.

The positioning system 10 is adapted for use on a conventional microscope 12 having an objective lens unit housing 14 of hollow cylindrical form. The microscope 12 is a surgical microscope of known construction, such as shown in U.S. Pat. 4,799,779, the details of which are not necessary for an understanding of the invention, and have been omitted for purposes of simplicity.

The lens unit housing 14 includes a lens unit 16 with an objective lens piece 18 affixed to an annular lens collar 20. The lens collar 20 is formed with exterior threads 24 that interengage with interior threads 26 formed on the lens unit housing 14. The threads 26 extend to an end portion 30 of the lens unit housing 14.

The positioning system 10 includes an adapter member 36 and a drape positioning member 38 shown in simplified form. The drape positioning member 38, which will be subsequently described in a more detailed form as shown in FIGS. 4–6, is attached to a microscope drape cover member 40.

The adapter member 36 is of annular shape and is preferably formed of a rigid material such as aluminum. The adapter member 36 includes opposite base ends 42 and 44 and an interior viewing space 46 defined by the inner diameter of the adapter member 36. The inner diameter of the adapter member 36 is substantially the same as the inner diameter of the lens collar 20. An exterior thread 48 formed on the adapter member 36 extends from the base end 42 to a projecting rim-like flange 50. The exterior thread 48 is engagable with the interior thread 26 of the lens unit housing 14.

An exterior tapered surface 54 extends from the base portion 44 of the adapter member 36 to a recess or engagement slot 56. The tapered surface 54, also referred to as a universal engaging surface, is in the form of a frustum of a cone and has an angle of taper between 15° and 22°, preferably 18.4°.

Figure 4:
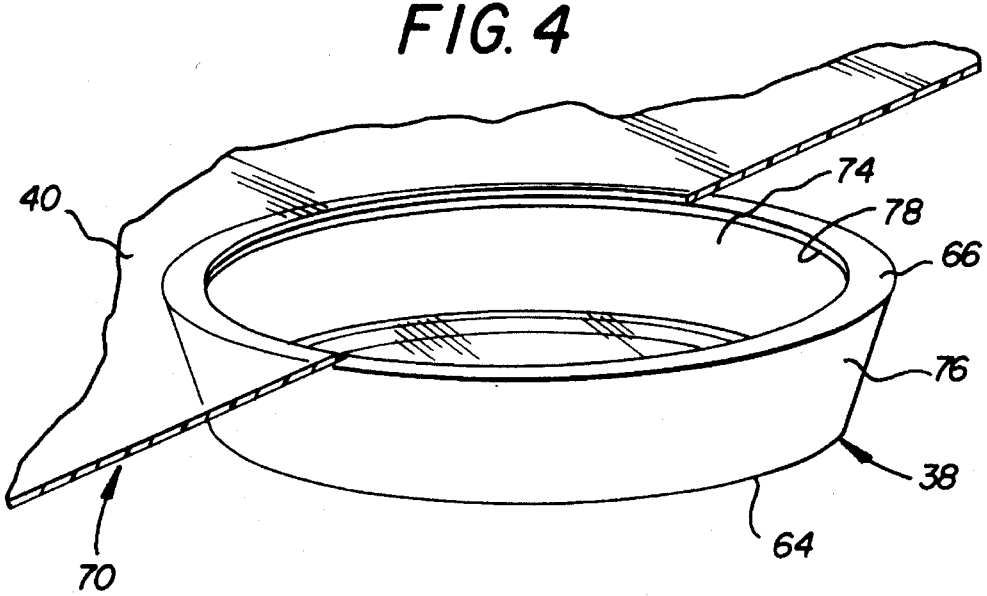
FIG. 4 is a fragmentary perspective view of a universal microscope drape with a universal engagement member.
Figure 5:
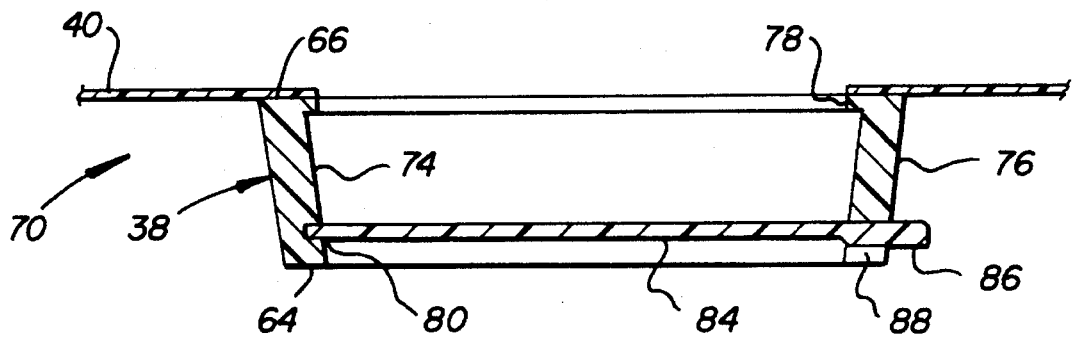
FIG. 5 is a sectional view of the universal engagement member.
Figure 6:
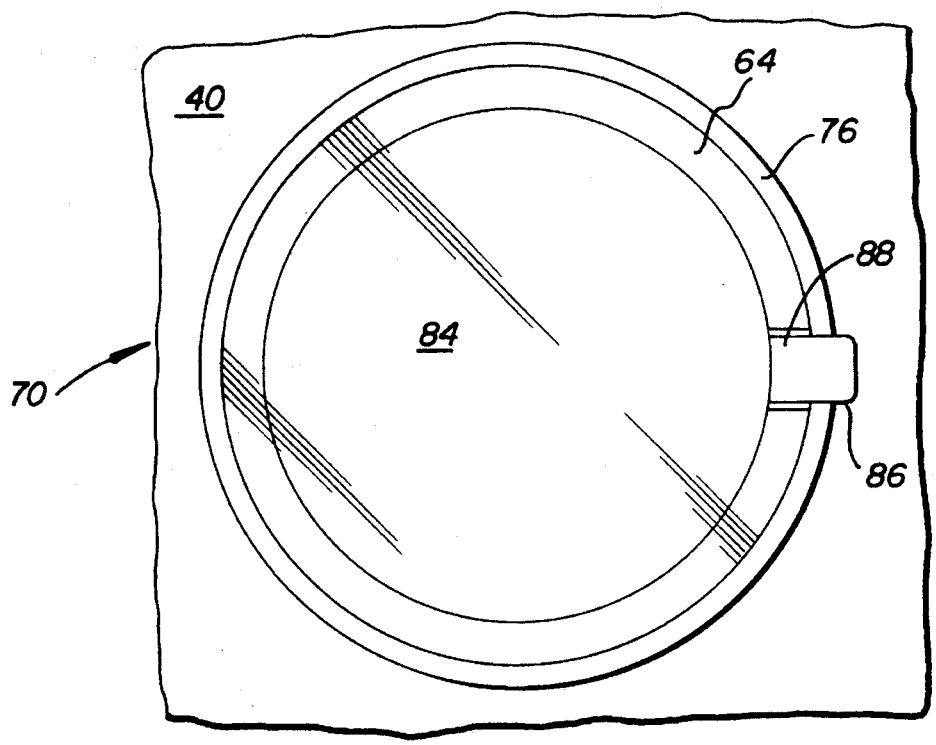
FIG. 6 is a plan view of the universal engagement member.

Referring to FIGS. 4–6, the microscope drape positioning member 38 is in the form of a hollow frustum of a cone, and is preferably formed of a soft, flexible and deformable thermoplastic rubber material such as sold under the trademark Krayton®, manufactured by Shell Chemical Co. The positioning member 38 includes a minor base end 64 and an opposite major base end 66. The microscope drape cover member 40, which is formed of a relatively thin transparent plastic material such as polyethylene, polypropylene or other suitable polymer or copolymer film, is joined to the positioning member 38 in any suitable known manner such as by bonding to the major base end 66 by heat welding for example. A microscope drape 70 which incorporates the positioning member 38 and the cover member 40 is of any suitable size and shape to cover the microscope 12.

A tapered inner surface 74 of the positioning member 38 is in the form of a conical frustum and has a taper angle that corresponds to the taper angle of the universal engagement surface 54 of the adapter member 36.

The tapered inner surface 74, also characterized as a universal engaging surface, is sized to frictionally receive the universal outer engaging surface 54 of the adapter member 36.

An outer surface 76 of the positioning member 38 is also in the form of a frustum of a cone and is substantially parallel to the inner surface 74. A lip portion 78 is formed at the major base end 66 and an annular groove 80 is formed in the tapered inner surface 74 proximate the minor base end 64, to receive a transparent plastic lens cover 84. The lens cover 84 includes a handle extension 86 that is aligned with a recess 88 at the minor base end 64.

The drape positioning member 38, as shown in FIGS. 1, 3, 7, 9, 10 and 12, is of simplified form for purposes of clarity, and omits the lens cover 84, the groove 80 and the recess 88.

In using the positioning system 10 for the microscope 12, the external threads 48 of the adapter member 36 are threaded into the internal threads 26 of the lens unit housing 14 to secure the adapter member 36 to the microscope 12. The adapter member 36 can be threaded to the lens housing 14 until the adapter rim 50, which includes a stop surface 52 engages the end portion 30 of the lens unit housing 14.

An outside surface 53 of the rim 50 can be knurled, if desired, to facilitate installation and removal of the adapter member 36 from the lens unit 16.

The microscope drape 70, which includes the drape positioning member 38 and the drape cover member 40, is installed on the microscope 12 by aligning the drape positioning member 38 with the previously installed adapter member 36. The drape positioning member 38 is mounted onto the adapter member 36 such that the inner tapered surface 74 embraces and grips the outer tapered surface 54 of the adapter member 36. The lip portion 78 of the drape positioning member 38 engages the slot 56 of the adapter member 36 to latch the drape positioning member 38 on the adapter member 36.

Referring to FIG. 5, the plastic lens cover 84 of the drape positioning member 38 is thus aligned with the lens piece 18 of the lens unit 16 to provide a clear field of view through the microscope 12. If desired, the plastic cover lens 84 can be removed from the positioning member 38 by pushing the tab portion 86 of the lens cover 84 away from the minor base end 64.

After a surgical procedure has been completed and removal of the microscope drape 70 is desired, the positioning member 38 is demounted from the adapter member 36 by, for example, pulling the drape 40 at the major base end 66 to pull the lip portion 78 away from the slot 56 of the adapter member 36. The adapter member 36 can be retained in the lens unit housing 14 for subsequent installations of disposable universal microscope drapes 70.

If the microscope drape 70 is to be used with a second microscope made by a different manufacturer but of the same general size as the microscope 12, a different adapter member than the adapter member 36 must be provided to securely engage with the lens unit housing of the second microscope.

Figure 7:
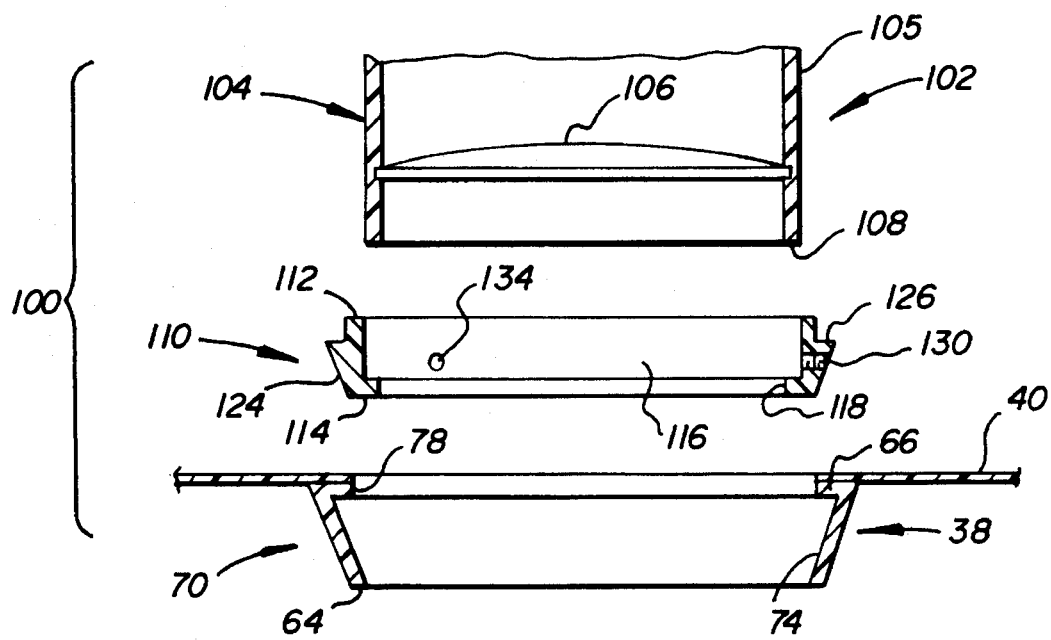
FIG. 7 is an exploded sectional view of a positioning system for a microscope drape, incorporating another embodiment of the invention, prior to installation on a microscope of a second manufacturer.

For example, another embodiment of a microscope drape positioning system for a second microscope of different manufacture than the microscope 12 is generally indicated by the reference number 100 in FIG. 7.

The positioning system 100 is adapted for use on a conventional microscope 102 having an objective lens unit housing 104 of hollow cylindrical form. Details of the microscope 102 which are not necessary for an understanding of the invention, have been omitted for purposes of simplicity.

The lens unit housing 104 includes a fixed lens unit 106 and a free end 108.

The positioning system 100 includes an annular adapter member 110 and the drape positioning member 38.

The adapter member 110, which can be formed of aluminum, includes opposite base ends 112 and 114 and an interior viewing space 116 defined by the inner diameter of the adapter member 110. The base end 114 includes an axially directed annular lip portion 118 that projects into the space 116. The inner diameter of the adapter member 110 between the lip 118 and the base end 112 is slightly larger than the outside diameter of the lens unit housing 104. The adapter member 110 can thus be disposed on the lens unit housing 104 such that the lip portion 118 of the adapter member 110 engages the free end 108 of the lens housing 104.

The adapter member 110 further includes an exterior tapered surface 124 similar to the exterior tapered surface 54 of the adapter member 36, extending from the base portion 114 to a ledge 126. The tapered surface 124 constitutes the universal engaging surface of the adapter member 110 and has the same angular specifications and dimensional magnitude as the tapered surface 54 of the adapter member 36. Set screw openings 130, 132 and 134 (FIG. 8) extend through the tapered surface 124 approximately 120° apart.

In using the positioning system 100 for the microscope 102, the adapter member 110 is secured to the lens unit housing 104 with set screws 136 (FIG. 9) that lock against the outer surface 105 of the lens housing 104.

The drape positioning member 38 of the universal microscope drape 70 is installed on the previously installed adapter member 110 such that the tapered surfaces 74 and 124 embrace and the lip portion 78 engages the ledge 126 to latch the drape positioning member 38 on the adapter member 110. Removal of the drape positioning member 38 from the adapter member 110 is accomplished in a manner similar to that described for the positioning system 10 or by accessing the major base end 66 of the drape positioning member 38 and pulling the lip portion 78 away from the ledge 126.

Figure 10:
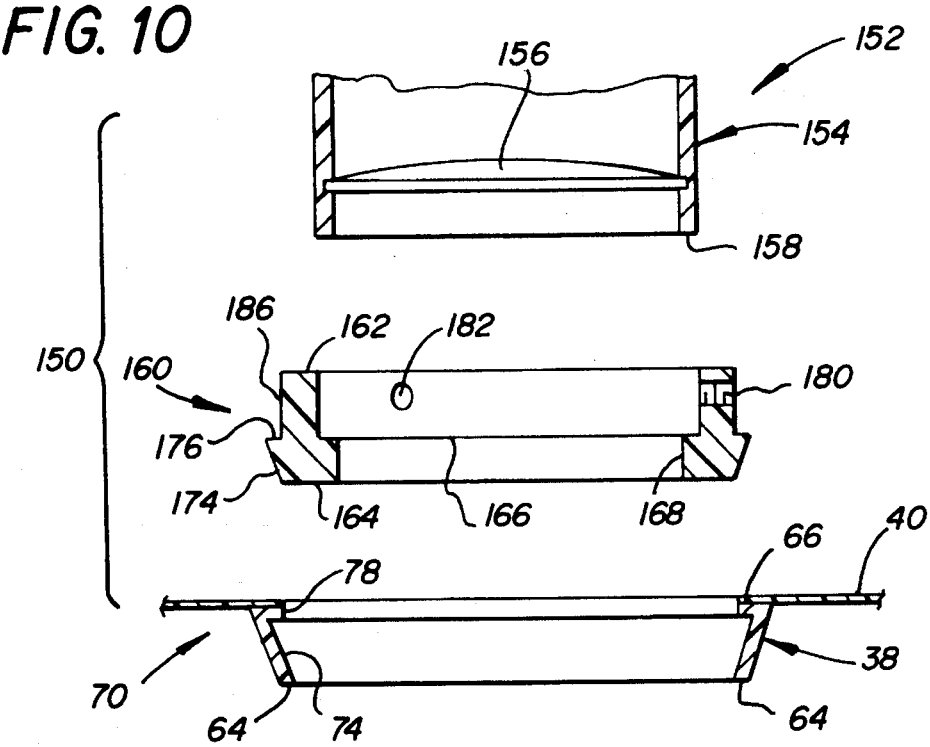
FIG. 10 is an exploded sectional view of a positioning system for a microscope drape, incorporating a further embodiment of the invention, prior to installation on a microscope of a third manufacturer.

A further embodiment of a microscope drape positioning system for a third microscope of different manufacture than the microscopes 12 and 102 is generally indicated by the reference number 150 in FIG. 10.

The positioning system 150 is adapted for use on a conventional microscope 152 having an objective lens unit housing 154 of hollow cylindrical form. Details of the microscope 152 which are not necessary for an understanding of the invention, have been omitted for purposes of simplicity.

The lens unit housing 154 includes a fixed lens unit 156 and a free end 158.

The positioning system 150 includes an annular adapter member 160 and the drape positioning member 38.

The adapter member 160, which is preferably formed of aluminum, includes opposite base ends 162 and 164 and an interior viewing space 166 defined by the inner diameter of the adapter member 160. The base end 164 includes an axially directed annular lip portion 168 that projects into the space 166. The inner diameter of the adapter member 166 between the lip 168 and the base end 162 is slightly larger than the outside diameter of the lens unit housing 154. The adapter member 160 is thus positionable on the lens unit housing 154 such that the lip portion 168 of the adapter member 160 engages the free end 158 of the lens housing 154.

Figure 11:
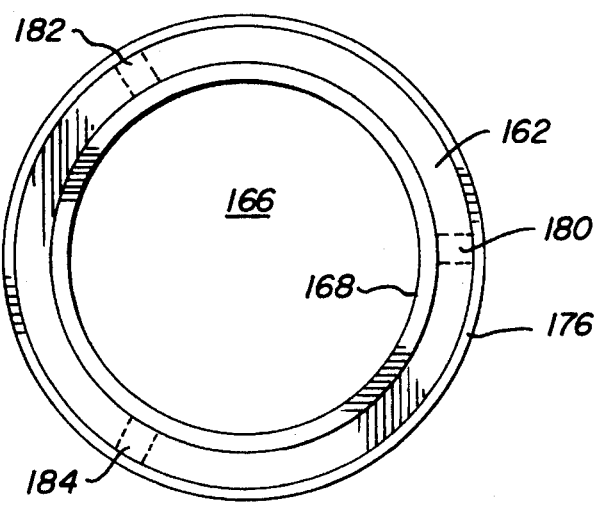
FIG. 11 is a plan view of the adapter member of the positioning system shown in FIG. 10; and, FIG. 12 is a sectional view of the positioning system as installed on a microscope.
Figure 12:
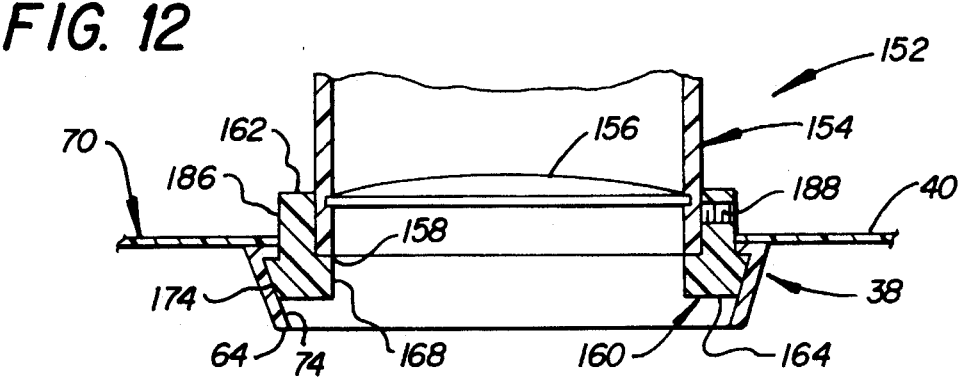

The adapter member 160 further includes an exterior tapered surface 174 similar to the exterior tapered surfaces 54 and 124 of the adapter members 36 and 110, extending from the base portion 164 to a ledge 176. The tapered surface 174 constitutes the universal engaging surface of the adapter member 160 and has the same angular specifications and dimensional magnitudes as the tapered surfaces 54 and 124 of the adapter members 36 and 110. Set screw openings 180, 182 and 184, approximately 120° apart (FIG. 11), extend through a neck portion 186 of the adapter member that is defined between the base end 162 and the ledge 176.

In using the positioning system 150 for the microscope 152, the adapter member 160 is secured to the lens unit housing 154 with set screws 188 (FIG. 12) that lock against the outer surface of the lens housing 154.

The drape positioning member 38 of the universal microscope drape 70 is installed on the previously installed adapter member 160 such that the tapered surfaces 74 and 174 embrace and the lip portion 78 engages the ledge 176 to latch the drape positioning member 38 on the adapter member 110. Removal of the drape positioning member 38 from the adapter member 110 is accomplished in a manner similar to that described for the positioning systems 10 and 100.

Thus, microscopes made by different manufacturers of the same general size and shape, equipped with adapter members such as the adapter members 36, 110 and 160 are capable of receiving the universal microscope drape 70 with the universal drape positioning member 38.

Some advantages of the invention evident from the foregoing description include a universal positioning system for a microscope drape that is adaptable to microscopes made by different manufacturers. The universal complementary tapered engaging surfaces of the adapter members and the drape positioning member ensure ease of application and ease of removal of the drape from the microscope. Since installation of the adapter members does not require disassembly of the lens unit housing, installation and removal of the adapter members are easily accomplished. Furthermore, once an adapter member is installed on a particular microscope, it can be reused over and over again. Thus the maintenance of a microscope drape inventory is substantially simplified since recourse to a universal microscope drape can satisfy most microscope draping requirements.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A system for positioning a microscope drape on a microscope having a lens housing with a lens unit comprising, an adapter member attachable to a microscope lens housing with a lens unit and having first engaging means for detachable engagement with said lens housing without connection to the lens unit such that the adapter member can be secured to the lens housing in tandem with the lens unit, said adapter member having second engaging means for detachable securement with a microscope drape, and a drape positioning member of a microscope drape having third engaging means detachably engagable with the second engaging means of said adapter member to secure the drape positioning member to the adapter member, whereby the microscope drape can be initially located on the adapter member when the adapter member is secured to the lens housing, said adapter member and said drape positioning member being of annular shape, said second engaging means of said adapter member being configured with the shade of an outer surface of a conical frustum and the third engaging means of the drape positioning member being configured with the shape of an inner surface of a hollow conical frustum adapted to embrace and grip the outer frustum surface of said adapter member.

2. The system of claim 1 including a plurality of adapter members, each of said adapter members having different first engaging means to engage with respectively different microscopes, and each of said adapter members having the same second engaging means whereby said drape positioning member can be universally engaged with the second engaging means of each of said plurality of adapter members such that the same said drape positioning member can be provided for said plurality of different microscopes.

3. The system of claim 1 wherein said drape positioning member is formed of a flexible resilient material and said adapter member is formed of a rigid non-resilient material.

4. The system of claims 3 wherein said drape positioning member has a minor base and a major base, the major base having an engagement lip for attachment to said adapter member.

5. The system of claim 1 wherein a transparent lens cover is detachably secured to the drape positioning member.

6. The system of claim 1 wherein said first engaging means include threads.

7. An adapter member for positioning a microscope drape on a microscope comprising a rigid adapter ring having means for detachable engagement with a microscope lens housing having a lens unit such that the adapter ring can be secured to the lens housing in tandem with the lens unit and without connection to the lens unit in a functional viewing position on the microscope, said adapter ring having a tapered outside surface in the form of a frustum of a cone for engagement with a complementary inside tapered surface of a microscope drape mounting sleeve to permit detachable securement of the mounting sleeve to said adapter ring whereby a microscope drape cover member that attaches to the mounting sleeve can be positioned on the microscope by engaging the mounting sleeve and the adapter ring after the adapter ring is interchanged with the lens unit.

8. The adapter member as claimed in claim 7 wherein said engaging means includes threads.

9. The adapter member as claimed in claim 7 wherein said engaging means includes set screws.

10. The adapter member as claimed in claim 9 wherein said set screws are provided through said tapered outside surface.

11. The adapter member as claimed in claim 9 wherein said adapter member has a non-tapered neck portion and said set screws are provided in said non-tapered neck portion.

12. A method of draping differently manufactured microscopes of comparable size comprising, a) detachably securing an adapter ring to a lens housing of the microscope in tandem with a lens unit on the lens housing such that the adapter ring is in a functional viewing position, b) providing the adapter ring with a tapered outside surface, c) forming an inside tapered surface on a flexible microscope drape positioning sleeve such that the inside tapered surface is complementary to the outside tapered surface on the adapter ring to permit detachable mounting of the drape positioning sleeve on the adapter ring, d) attaching the flexible positioning sleeve to a microscope drape cover member to form a universal microscope drape, and e) locating the microscope drape positioning sleeve on the adapter ring and draping the microscope with the drape cover member.

13. The method of claim 12 including securing the adapter ring to the lens housing by threading.

14. The method of claim 12 including securing the adapter ring to the lens housing with set screws.

15. The method of claim 12 wherein in the securing step, the adapter ring is free from connection with the lens unit.

16. The method of claim 12, including providing separate adapter rings engageable with selected differently manufactured microscopes at their lens housing for attachment to the lens housing in tandem with the lens unit in the lens housing, and forming each adapter ring with the same outside tapered surface to match the inside tapered surface of the positioning sleeve whereby the universal microscope drape cover member positioning sleeve can be secured to the adapter ring of each differently manufactured microscope to permit use of the universal microscope drape on the differently manufactured microscopes.

17. A system for positioning a microscope drape on a microscope having a lens housing with a lens unit comprising, a) an adapter member attachable to a microscope lens housing with a lens unit and having first engaging means including set screws for detachable engagement with said lens housing without connection to the lens unit such that the adapter member can be secured to the lens housing in tandem with the lens unit, said adapter member having second engaging means including set screws for detachable securement with a microscope drape, and b) a drape positioning member of a microscope drape having third engaging means detachably engagable with the second engaging means of said adapter member to secure the drape positioning member to the adapter member, whereby the microscope drape can be initially located on the adapter member when the adapter member is secured to the lens housing.

18. The system of claim 17 wherein said adapter member has a non-tapered neck portion and said set screws are provided in said non-tapered neck portion.

* * * * *

UNITED STATES PATENT AND TRADEMARK OFFICE
CERTIFICATE OF CORRECTION

PATENT NO. : 5,467,223
DATED : November 14, 1995
INVENTOR(S) : Cleveland, Jr., et al.

It is certified that error appears in the above-identified patent and that said Letters Patent is hereby corrected as shown below:

Column 7, line 43, after "configured with the", delete "shade" and insert -- shape --.

Column 7, line 61, after "system of", delete "claims" and insert -- claim --.

Signed and Sealed this

Second Day of April, 1996

Attest:

BRUCE LEHMAN

Attesting Officer

Commissioner of Patents and Trademarks